United States Patent
Adams

(10) Patent No.: US 7,128,574 B2
(45) Date of Patent: Oct. 31, 2006

(54) DENTAL ALIGNMENT INSTRUMENT

(76) Inventor: Suzanne Adams, 20303 Starry St., Orlando, FL (US) 32833

( * ) Notice: Subject to any disclaimer, the term of this patent is extended or adjusted under 35 U.S.C. 154(b) by 0 days.

(21) Appl. No.: 11/068,311

(22) Filed: Feb. 24, 2005

(65) Prior Publication Data

US 2006/0188839 A1    Aug. 24, 2006

(51) Int. Cl.
*A61C 19/04*    (2006.01)
(52) U.S. Cl. .......................... 433/68; 433/54
(58) Field of Classification Search ............ 433/68–71, 433/54, 37, 38, 43, 44
See application file for complete search history.

(56) References Cited

U.S. PATENT DOCUMENTS

| | | | |
|---|---|---|---|
| 2,701,915 A * | 2/1955 | Page | 433/69 |
| 2,722,744 A * | 11/1955 | Wagner | 433/43 |
| 3,693,260 A | 9/1972 | Hernandez | |
| 4,306,861 A * | 12/1981 | Dickson | 433/69 |
| 4,422,849 A | 12/1983 | Diamond | |
| 4,455,137 A | 6/1984 | Diamond | |
| 4,474,555 A | 10/1984 | Diamond | |
| 4,908,949 A | 3/1990 | Jaccard | |
| 5,069,619 A * | 12/1991 | Frisbie | 433/72 |
| 5,154,609 A * | 10/1992 | George | 433/68 |
| 5,176,515 A | 1/1993 | Andrews | |
| 5,738,517 A | 4/1998 | Keller | |
| 6,109,917 A | 8/2000 | Lee et al. | |
| 6,582,931 B1 * | 6/2003 | Kois et al. | 435/56 |
| 2003/0049585 A1 * | 3/2003 | Severance | 433/29 |

FOREIGN PATENT DOCUMENTS

DE    4221510 A1 *    1/1994

* cited by examiner

*Primary Examiner*—Ralph A. Lewis
*Assistant Examiner*—Casey Donahoe
(74) *Attorney, Agent, or Firm*—William M. Hobby, III

(57) ABSTRACT

A handheld dental instrument has a horizontal level indicator and a vertical midline angle marker pin mounted on a bite line plate. The bite line plate has an arcuate front and a pair of protruding positioning pins. The bite line plate is rotatably mounted to a handle. The dental device is used in the formation of custom fitted lab fabricated dental prosthesis to improve dental bite registration recording of a patient's horizontal and vertical angles by the dentist and transferred to the dental lab technician to permit the formation of a prosthesis.

4 Claims, 2 Drawing Sheets

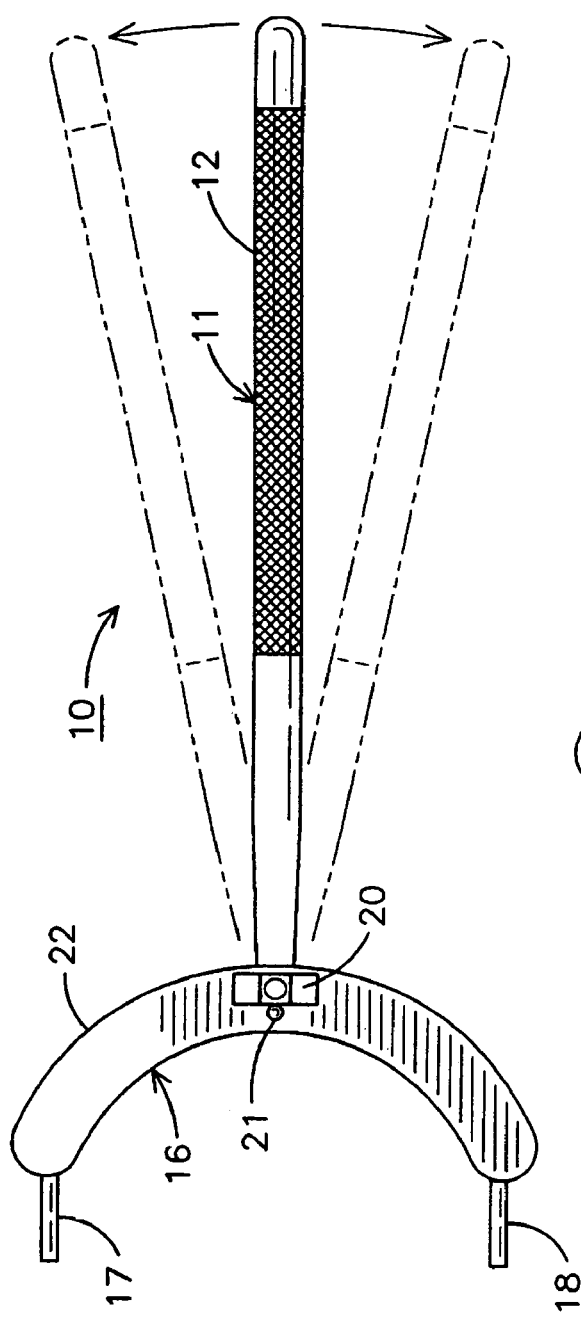

DENTAL ALIGNMENT INSTRUMENT

BACKGROUND OF THE INVENTION

This invention relates to dental devices and procedures used in the formation of custom fitted dental prosthesis and especially to a dental alignment instrument for a dentist or a dental lab technician to acquire the proper bite angle of a patient.

Dental prostheses, such as crowns, bridges, veneers, dentures and related dental procedures are well known in the art for restoring damaged or missing teeth within the mouth of a patient. In general terms, the area to be restored is initially prepared by the dentist, such as by reducing a damaged tooth by drilling and shaping procedures, to form a suitable base adapted to receive and support a prosthetic crown. The prepared area including adjacent and opposing tooth and gum structures is then replicated by means of a dental impression defined typically by a curable vinyl elastomer or the like carried on a suitably shaped impression tray which is placed into the patient's mouth for the duration of a short cure cycle. The dental impression is then used to form the appropriate mold or molds from which the desired dental prosthesis is formed, normally from a castable gold alloy or the like. Other types of dental prostheses may require an imprint of the patient's bite registration.

The dental impression or bite imprint is commonly fitted into a dental articulator in the course of producing the requisite mold or molds for the final prosthesis. However, in accordance with standard dental laboratory procedures, the dental articulator is oriented horizontally to correspondingly reproduce a horizontal patient bite line or angle. Unfortunately, the actual bite angle in many patients deviates from a horizontal plane. As a result, the prosthesis is shaped for precision custom fit according to a horizontal patient bite line which does not in fact exist. When the dentist attempts to place the prosthesis into the patient's mouth, an improper or unsatisfactory fit is recognized. Since most bite angle deviations are relative small, the dentist normally tries to remedy the prosthesis misfit by trial and error grinding of the prosthesis. This approach can be extremely costly to the dentist by substantially increasing the time needed for proper prosthesis fit and placement. Moreover, and more importantly, trial and error attempts to reshape the prosthesis often result in a poor fit and resultant poor service life and patient dissatisfaction.

In the past, dental appliances have been proposed particularly in the field of orthodontics for use in measuring the patient's bite line or angle. However, such appliances have been relatively costly and difficult to use, and further have not provided a bite angle indication which can be satisfactorily communicated to and reproduced at a dental laboratory located typically at a different facility. Accordingly, in spite of the aforementioned problems attributable to bite angle variations, the general dental practice has been to ignore the problem or otherwise accommodate bite angle deviations by estimation and/or trial and error procedures.

Prior U.S. Patents relating to dental instruments can be seen in the Frisbie U.S. Pat. No. 5,069,619 for a dental impression tray with a level indicator which is provided with a level indicator to indicate a patient's bite angle. The impression tray is placed into the mouth of the patient and holds the level indicator to indicate the patient's bite angle, particularly with respect to deviations from a horizontal plane. The bite angle information is used subsequently in dental laboratory procedures to accommodate the specific bite angle in the formation of a dental prosthesis. In the Lee et al. U.S. Pat. No. 6,109,917, a system for establishing a reference plane for dental casts is provided so that the patient's teeth can be oriented to a horizontal reference plane. The apparatus includes a face bow with an adjustable nasion relator assembly and a level gauge and a bite fork.

In the Diamond U.S. Pat. Nos. 4,474,555 and 4,422,849 and 4,455,137, a dental instrument and method for positioning an orthodontic bracket is disclosed and has a housing on which is positioned an arm that includes a means for releasably holding the orthodontic bracket and includes level indicating means used for displaying the extend of inclination of the arm with respect to a predetermined plane. The Hernandez U.S. Pat. No. 3,693,260 is a multi-purpose adjustable occlusal fork. A horizontal bite plate support is combined with a dental articulator which has a calibrated vertical post member which has a connection to support a face bow in a position to establish the location of a patient's transverse mandible hinge axis. The Jaccard Patent No. 4,908,949 is an air bubble level for portable tools. The Keller Patent No. 5,738,517 is an apparatus and method of fixed reference examination of dental patients and includes a bubble level carried by a face bow. The Andrews Patent No. 5,176,515 is a dental treatment method and apparatus which includes a level.

The present invention is a dental device and procedure used in the formation of custom fitted lab fabricated dental prosthesis, such as crowns, fixed bridges, removable dentures, and interior veneers. The dental instrument is used to improve dental bite registration accordingly to the patient's horizontal and vertical angles by the dentist and transferred to the lab technician to permit the formation of a prosthesis. A lab technician can continuously check the horizontal and vertical line angles while fabricating the dental appliance.

SUMMARY OF THE INVENTION

A handheld dental instrument is provided having a horizontal level indicator and a vertical midline angle marker pin mounted perpendicular to a bite line plate having an arcuate front and protruding positioning pin which is rotatably mounted to a handle. The dental device is used in the formation of custom fitted lab fabricated dental prosthesis, such as crowns, fixed bridges, removable dentures, and interior veneers, and provides improvements in the dental bite registration recording of the patient's horizontal and vertical angles by the dentist and transferred to the dental lab technician to permit the formation of a prosthesis. The dental lab technician can continually check the horizontal and vertical line angles while fabricating the dental appliance thereby eliminating guessing of the incisal edges and midline of the interior teeth so that they are placed at a proper angle. The dental instrument is utilized by the dentist and the dental lab technician to accurately acquire the proper bite angle of a patient and any deviations from the horizontal plane. The dentist places the instrument on a bite registration stick and obtains the bite relation in regard to the patient's pupillary line angle and a true horizontal line angle. This registration can then be used by the dental lab technician when producing the requisite mold or molds for the final prosthesis.

The dental alignment instrument for use in stick bite registration and in the fabrication of a dental prosthesis has an elongated handle for holding the instrument. A bite line plate has an arcuate front edge and is rotatably mounted on the handle. The bite line plate has a pair of positional pins protruding therefrom on either side of the arcuate front edge for positioning the bite line plate. A level indicator is mounted on the bite line plate for displaying the horizontal level of the dental instrument. A 90 degree interproximal alignment pin is mounted perpendicular on the bite line plate or used as a vertical midline reference. The dentist and dental lab technician can thereby better determine a patient's bite line in formulating a dental prosthesis. The dentist uses the dental alignment instrument in making a dental impression or bite imprint which is then commonly fitted into a dental articulator for producing the mold or a final prosthesis. The dental lab technician is then able to use the same instrument in shaping the prosthesis according to a horizontal patient bite line to avoid bite angle deviations.

BRIEF DESCRIPTION OF THE DRAWINGS

Other objects, features, and advantages of the present invention will be apparent from the written description and the drawings in which:

FIG. 3 is a top elevation of a dental alignment instrument of FIGS. 1 and 2 illustrating the rotation between the bite line plate and the handle; and FIG. 4 is a bottom elevation of the dental instrument of FIGS. 1–3.

DETAILED DESCRIPTION OF THE PREFERRED EMBODIMENTS

Figure 1:
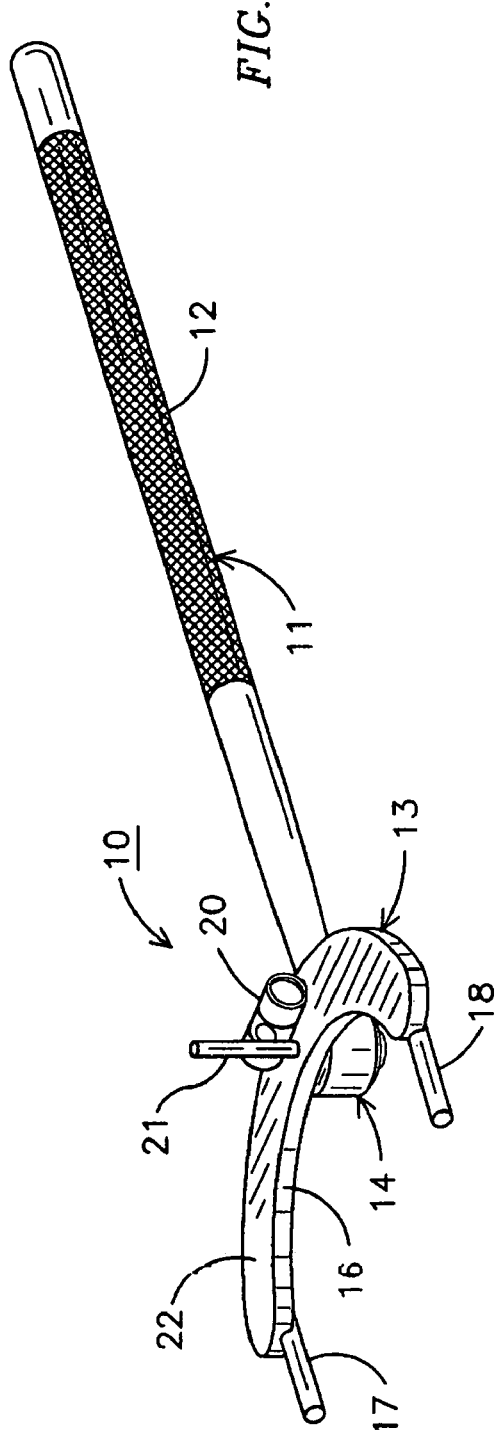
FIG. 1 is a perspective view of a dental alignment instrument in accordance with the present invention.

Referring to the drawings, FIGS. 1–4, a dental alignment instrument 10 has a handle 11 having knurling 12 on the handle. The handle has mounted on the end thereof a bite line plate 13 which is rotatably attached to the handle 11 with a hinge 14 having a hinge pin 15. The bite line plate 13 can be seen as having an arcuate front edge 16 and as having a generally arcuate shape but it will be clear that the rear edge of the bite line plate does not have to be of any particular shape. A pair of positioning pins 17 and 18 are mounted to either side of the bite line plate 13 at each opposite end of the arcuate edge 16. The bite line plate also has a horizontal bubble level 20 mounted thereto and has a perpendicularly mounted interproximal alignment pin 21 attached to the center of the bite line plate directly in the center of the arcuate edge 16 and extending 90 degrees from the top surface 22 of the bite plate 13. The interproximal alignment pin 21 is used for determining the vertical midline reference while the level 20 is used to maintain a horizontal level.

Figure 2:
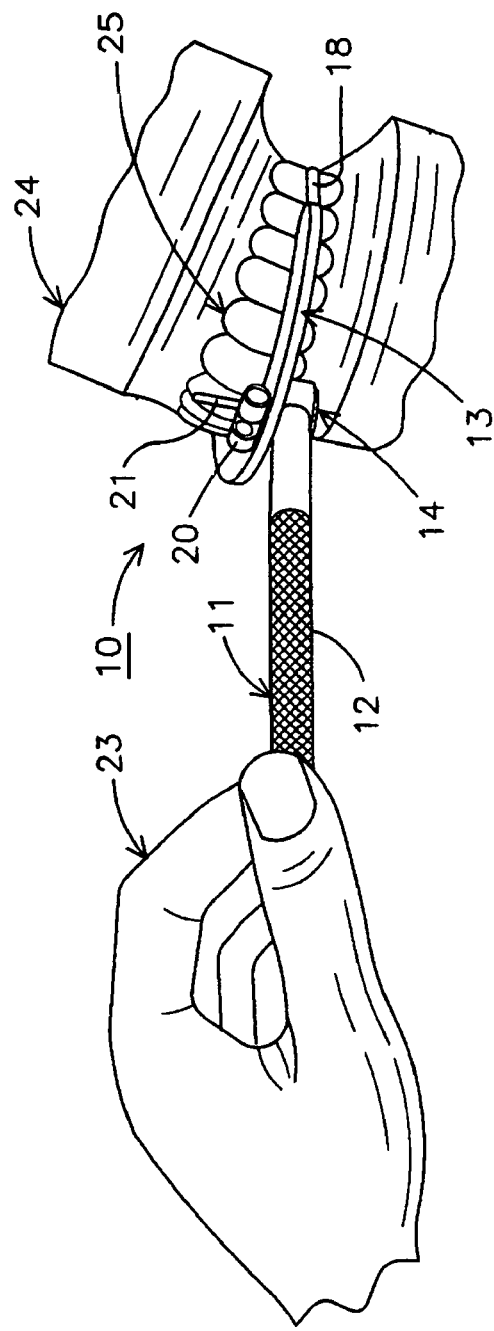
FIG. 2 is a perspective view of the dental alignment instrument of FIG. 1 being used to determine a bite line.

In FIG. 2, a dental lab technician's hand 23 is holding the handle 11 of the dental alignment instrument 10 and has positioned the positioning pins 17 and 18 on the sides of a prosthesis 24, teeth 25, with the arcuate front edge 16 extending around the arcuate placement of the teeth 25. The dental lab technician is able to determine a vertical midline reference with the interproximal alignment pin 21 and can maintains a horizontal plane using the bubble level 20 to determine a reference line.

The lab technician can rotate the handle 11 relative to the bite line plate 13 while the dental impression is in a dental articulator so that parts of the frame of the dental articulator do not interfere with the use of the dental alignment instrument. Similarly, the dentist can also utilize the dental alignment instrument while making a dental impression or bite imprint from a patient. It can also use the dental alignment instrument when placing the prosthesis in the patient's mouth to provide a satisfactory fit and to thereby avoid having to remedy a prosthesis misfit by grinding of the prosthesis. Thus, the dental alignment instrument can be used to determine the vertical midline reference using the interproximal alignment pin 21 which is placed perpendicular to the bite line plate 13 adjacent the level 20 so that when the bite line plate 13 is at a horizontal level, as shown by the level 20, the pin 21 is always at 90 degrees or vertical from a horizontal plane.

The dental alignment instrument can be utilized by either a dentist or a dental lab technician to accurately align the proper bite angle of a patient and to indicate any deviations from a horizontal plane. The dentist places the instrument on a bite registration stick and obtains the bite relationship in regards to the patient's pupillary line angle to determine a true horizontal line angle. The dentist can also mark the 90 degree vertical midline interproximal reference at the same time. The registration can then be used by the dental lab technician to accurately produce the requisite mold or molds for a final prosthesis in a dental articulator when the prosthesis is being shaped or positioned for custom fit according to a horizontal bite line. This allows a dentist to place the prosthesis in the patient's mouth with a more proper fit and to avoid correcting angle deviations and misfits by trial and error grinding of the prosthesis.

It should be clear at this time that a dental alignment instrument has been provided which can be utilized by both the dentist and a dental lab technician in the making of a dental prosthesis. However, the present invention should not be considered as limited to the forms shown which are to be considered illustrative rather than restrictive.

I claim:

1. A dental alignment instrument comprising:
    an elongated handle having two end portions;
    a bite line plate having an arcuate front edge and having a hinge pin for hingedly attaching said bite line to one end portion of said handle, said bite line plate having a pair of positional pins protruding therefrom on either side of said arcuate front edge; and
    a level indicator mounted on said bite line plate for displaying the horizontal level of said dental instrument;
    whereby a dentist and dental lab technician can better determine a patient's bite line in formulating a dental prosthesis.

2. The dental alignment instrument in accordance with claim 1 having an interproximal alignment pin extending perpendicular to the top surface of said bite line plate for determining a vertical midline reference.

3. The dental alignment instrument in accordance with claim 2 in which said bite line plate is generally arcuate.

4. The dental alignment instrument in accordance with claim 2 in which said elongated handle is partially knurled.

* * * * *